(12) United States Patent
Hendrix et al.

(10) Patent No.: US 7,154,607 B2
(45) Date of Patent: Dec. 26, 2006

(54) FLAT SPECTRUM ILLUMINATION SOURCE FOR OPTICAL METROLOGY

(75) Inventors: James Lee Hendrix, Livermore, CA (US); David Y. Wang, Fremont, CA (US); David M. Aikens, Chester, CT (US); Lawrence Rotter, Pleasanton, CA (US); Joel Ng, San Leandro, CA (US)

(73) Assignee: Therma-Wave, Inc., Fremont, CA (US)

( * ) Notice: Subject to any disclaimer, the term of this patent is extended or adjusted under 35 U.S.C. 154(b) by 381 days.

(21) Appl. No.: 10/700,086

(22) Filed: Nov. 3, 2003

(65) Prior Publication Data
US 2004/0150828 A1 Aug. 5, 2004

Related U.S. Application Data

(60) Provisional application No. 60/423,599, filed on Nov. 4, 2002.

(51) Int. Cl.
*G01N 21/55* (2006.01)

(52) U.S. Cl. .................................................. 356/445

(58) Field of Classification Search ................ None
See application file for complete search history.

(56) References Cited

U.S. PATENT DOCUMENTS

| 5,257,086 A | * | 10/1993 | Fateley et al. ............... 356/328 |
| 5,736,410 A | * | 4/1998 | Zarling et al. ............... 436/172 |
| 6,587,485 B1 | * | 7/2003 | Renlund et al. .............. 372/20 |
| 6,788,404 B1 | | 9/2004 | Lange ..................... 356/237.2 |
| 2002/0001080 A1 | * | 1/2002 | Miller et al. ................ 356/326 |
| 2002/0196437 A1 | * | 12/2002 | Tandon et al. .............. 356/320 |
| 2003/0030799 A1 | | 2/2003 | Chen et al. ................. 356/300 |
| 2003/0169425 A1 | | 9/2003 | Hendrix et al. ............. 356/445 |
| 2004/0012774 A1 | | 1/2004 | Lange ..................... 356/237.1 |

* cited by examiner

*Primary Examiner*—Michael P. Stafira
(74) *Attorney, Agent, or Firm*—Stallman & Pollock LLP

(57) ABSTRACT

A flat spectrum illumination source for use in optical metrology systems includes a first light source generating a visible light beam and a second light source generating an ultraviolet light beam. The illumination source also includes an auxiliary light source generating a light beam at wavelengths between the visible light beam and the ultraviolet light beam. The three light beams are combined to provide a broadband probe beam that has substantially even illumination levels across a broad range of wavelengths. Alternately, the illumination source may be fabricated as an array of light emitting diodes selected to cover a range of separate wavelengths. The outputs of the LED array are combined to produce the broadband probe beam.

14 Claims, 6 Drawing Sheets

Wavelength
(angstroms)

Wavelength
(angstroms)

Wavelength
(angstroms)

Fig. 4A
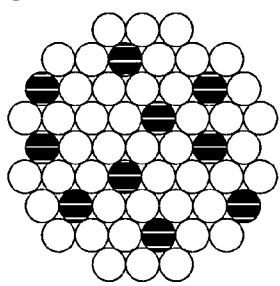
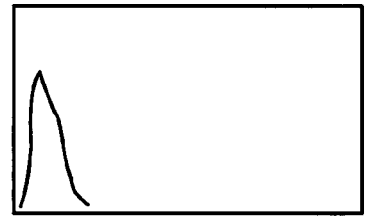
Fig. 5A
Fig. 4B
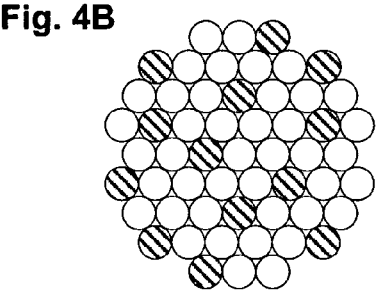
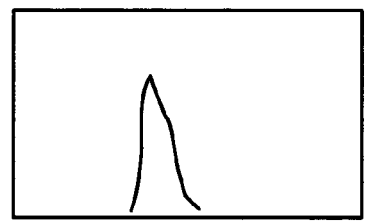
Fig. 5B
Fig. 4C
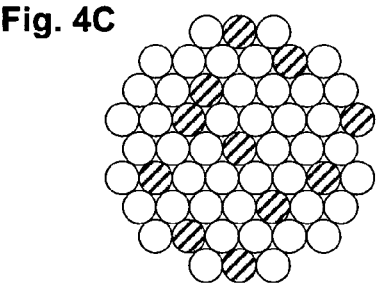
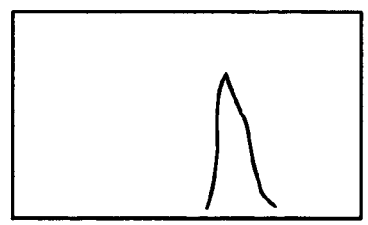
Fig. 5C
Fig. 4D
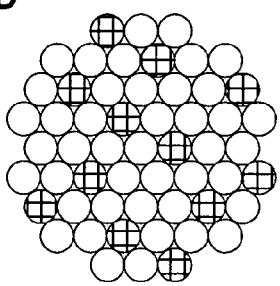
Fig. 5D

FLAT SPECTRUM ILLUMINATION SOURCE FOR OPTICAL METROLOGY

PRIORITY CLAIM

The present application claims priority to U.S. Provisional Patent Application Ser. No. 60/423,599, filed Nov. 4, 2002, which is incorporated in this document by reference.

TECHNICAL FIELD

The subject invention relates to devices used to create probe beams within optical metrology systems. In particular, the present invention relates to systems for creating probe beams having uniform illumination over a wide range of wavelengths.

BACKGROUND OF THE INVENTION

As semiconductor geometries continue to shrink, manufacturers have increasingly turned to optical techniques to perform non-destructive inspection and analysis of semiconductor wafers. Techniques of this type, known generally as optical metrology, operate by illuminating a sample with an incident field (typically referred to as a probe beam) and then detecting and analyzing the reflected energy. Ellipsometry and reflectometry are two examples of commonly used optical techniques. For the specific case of ellipsometry, changes in the polarization state of the probe beam are analyzed. Reflectometry is similar, except that changes in intensity are analyzed. Scatterometry is a specific type of optical metrology that is used when the structural geometry of a sample creates diffraction (optical scattering) of the probe beam. Scatterometry systems analyze diffraction to deduce details of the structures that cause the diffraction to occur.

Various optical techniques have been used to perform optical scatterometry. These include broadband spectroscopy (U.S. Pat. Nos. 5,607,800; 5,867,276 and 5,963,329), spectral ellipsometry (U.S. Pat. No. 5,739,909) single-wavelength optical scattering (U.S. Pat. No. 5,889,593), and spectral and single-wavelength beam profile reflectance and beam profile ellipsometry (U.S. Pat. No. 6,429,943). Scatterometry, in these cases generally refers to optical response information in the form of diffraction orders produced by periodic structures (e.g., gratings on a wafer). In addition it may be possible to employ any of these measurement technologies, e.g., single-wavelength laser BPR or BPE, to obtain critical dimension (CD) measurements on non-periodic structures, such as isolated lines or isolated vias and mesas. The above cited patents and patent applications, along with PCT Application WO03/009063, US Application 2002/0158193, US Application 2003/0147086, US Application 2001/0051856 A1, PCT Application WO 01/55669 and PCT Application WO 01/97280 are all incorporated herein by reference.

Most metrology techniques (including those just described) may be performed using monochromatic or polychromatic light. In the case where polychromatic light is used, the interaction between the probe beam and the subject is analyzed as a function of wavelength. In many cases, this increases the accuracy of the analysis. As shown in FIG. 1A, a representative implementation of an ellipsometer or reflectometer configured to perform this type of polychromatic analysis includes a broadband light source. The light source creates a polychromatic probe beam that is focused by one or more lenses on a subject. The subject reflects the probe beam. The reflected probe beam passes through an aperture and another series of one or more lenses to a detector. A processor analyzes the measurements made by the detector.

As shown in FIG. 1B, the broadband light source is a combination of two different sources: a visible light source and a UV source. The visible light source is typically a tungsten lamp and the UV source is typically a deuterium lamp. The outputs of the two lamps are combined using a beam combiner. Prior art beam combiners are usually formed by depositing a very thin partially transparent metal film, such as aluminum on a substrate. The surface of the film is coated with a protective layer of silicon dioxide or magnesium fluoride. A notable example of a UV to visible beam combiner is a 50/50 beam splitter. The output of the beam combiner is the probe beam produced by the broadband light source. The combination of the two separate lamps increases the spectrum of the probe beam beyond what would be practical using a single source.

Unfortunately, the use of broadband light sources of the type shown in FIG. 1 has known drawbacks. As shown in FIG. 1C, the resulting probe beam is not constant as a function of wavelength. Instead, there is a tendency for illumination levels to be weak for wavelengths that fall between the outputs of the two separate lamps. For this reason, broadband ellipsometers and reflectometers are typically configured to electronically compensate for the uneven nature of their probe beams. For many applications this produces acceptable results. This is not the case for the low illumination levels required by advanced systems. In these cases, the electronic compensation process actually masks data that would otherwise reach the detector for analysis. This degrades detector performance and reduces overall sensitivity.

For these reasons and others, a need exists for improved devices for creating probe beams having uniform illumination levels across a range of useful wavelengths. This need is especially important for metrology tools that require the combination of multiple illumination sources to create wide spectrum polychromatic probe beams.

BRIEF DESCRIPTION OF THE DRAWINGS

FIGS. 4A through 4D show the output of the LED array of FIG. 3A for a series of different monochromatic modes.

FIGS. 5A through 5D graph illumination as a function of wavelength for the monochromatic mode shown in FIGS. 4A through 4C.

DETAILED DESCRIPTION OF THE PREFERRED EMBODIMENTS

Figure 1A:
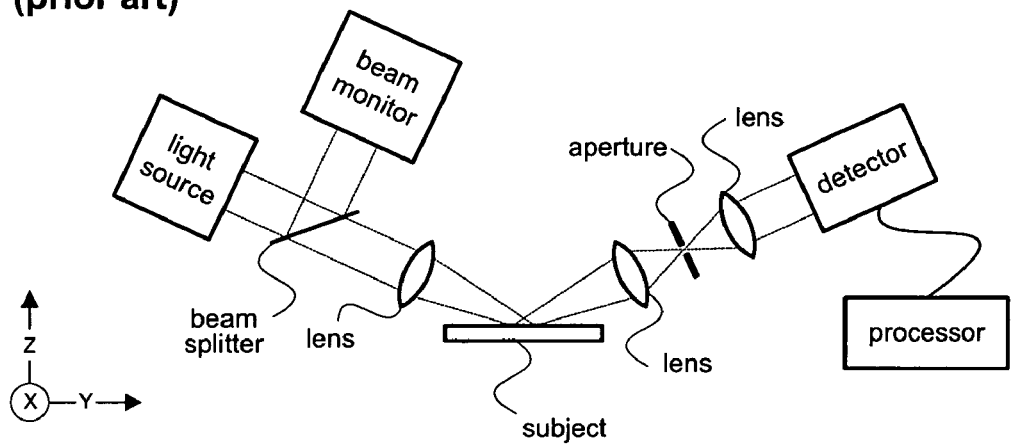
FIG. 1A is a diagram of prior art optical metrology system.
Figure 1B:
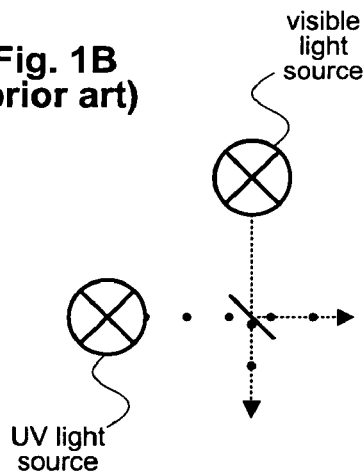
FIG. 1B is a diagram of prior art illumination source as used in the optical metrology system of FIG. 1A.
Figure 1C:
FIG. 1C is a graph showing illumination as a function of wavelength for the illumination source of FIG. 1B.
Figure 2A:
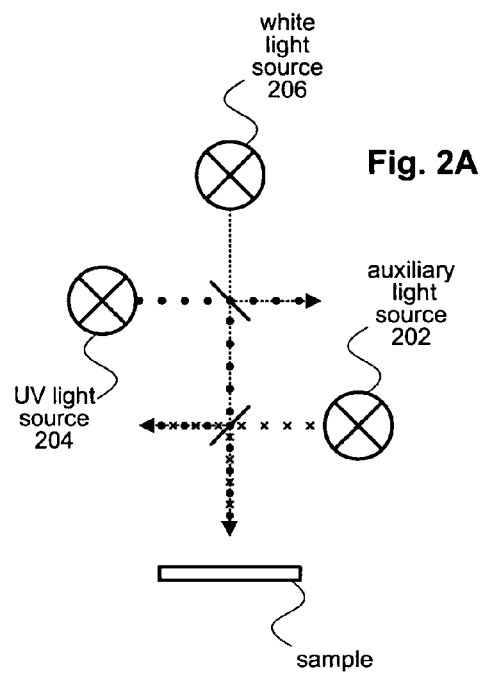
FIG. 2A is a diagram of a flat spectrum illumination source as provided by a first embodiment of the present invention.
Figure 2B:
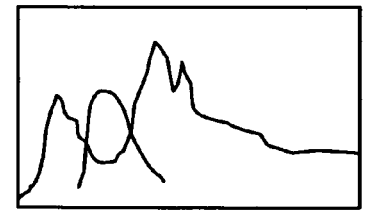
FIG. 2B is a graph showing illumination as a function of wavelength for the separate lamps used in the illumination source of FIG. 2A.
Figure 2C:
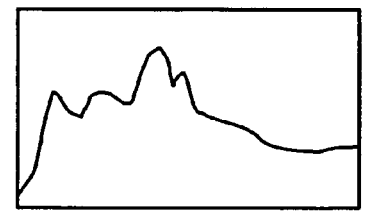
FIG. 2C is a graph showing illumination as a function of wavelength for the combined lamps used in the illumination source of FIG. 2A.

The present invention includes a flat spectrum illumination source for optical metrology. As shown in FIG. 2A, an embodiment of the present invention includes uses an auxiliary light source 202 to augment the light deficiency between a UV source 204 (e.g., deuterium lamp) and a white light source 206 (e.g., tungsten lamp). Auxiliary light source 202 is typically a light emitting diode or diode array. As shown in FIGS. 2B and 2C, this approach adds light to the combined spectrum in the area in which the spectrum is lowest and thus flattens out the overall spectrum of the resulting probe beam.

Figure 2D:
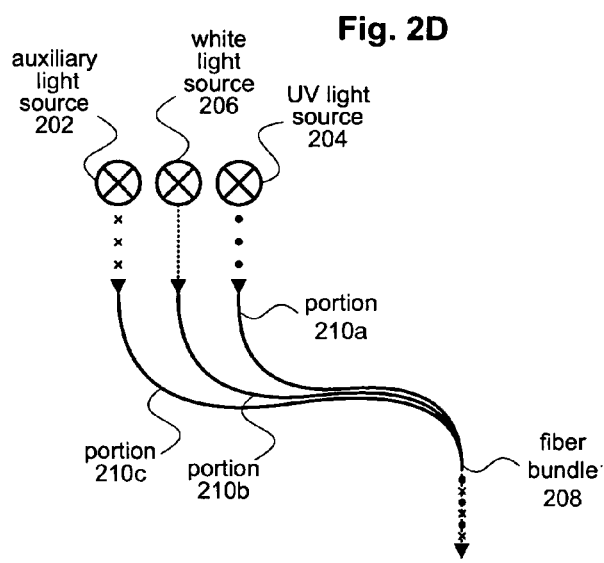
FIG. 2D is a diagram of a flat spectrum illumination source of FIG. 2A using an optical fiber for beam combination.
Figure 2E:
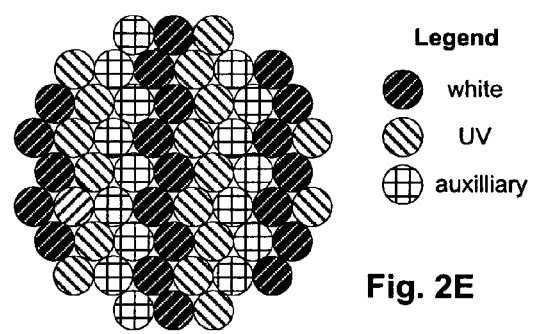
FIG. 2E is a diagram showing interleaving of three different illumination sources within the optical fiber of FIG. 2D.

In FIG. 2A, the output of auxiliary light source 202 is added to the probe beam using a beam splitter. Alternately, as shown in FIG. 2D, the output of the separate sources 202, 204 and 206 may be combined into a single fiber optic or fiber optic bundle 208. Typically, this is done by directing different portions of a fiber bundle (labeled 210a through 210c) to receive the outputs of the separate sources 202, 204 and 206. Portions 210 can be selected so that their individual fibers are interleaved within fiber optic bundle 208. Interleaving of this type is show in FIG. 2E.

Figure 2F:
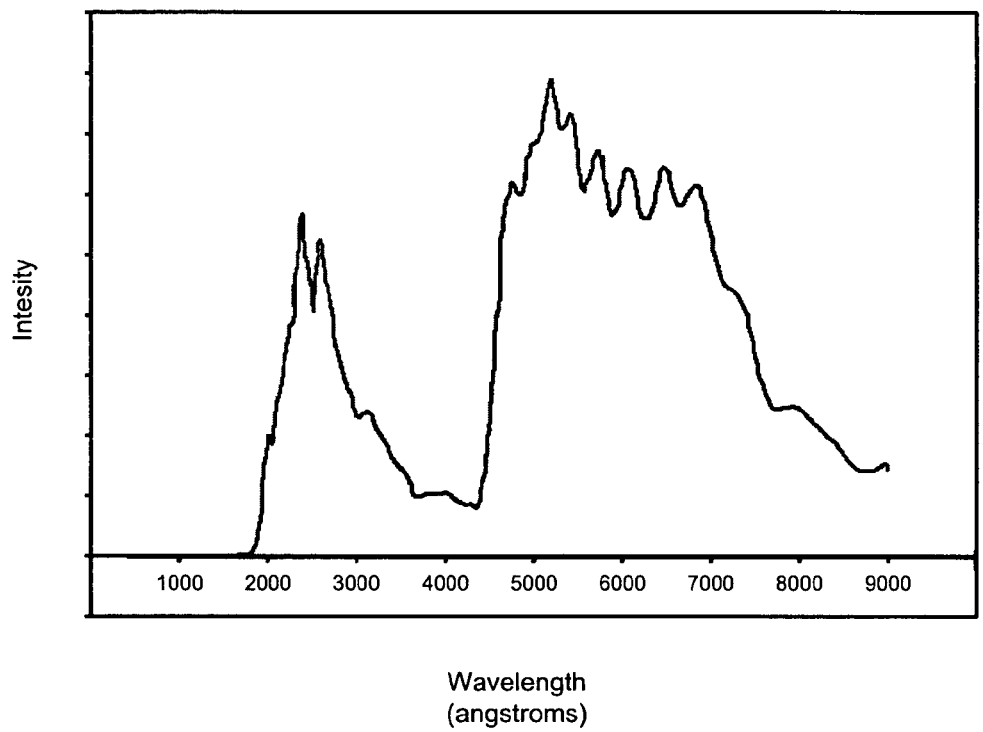
FIG. 2F is a graph showing illumination as a function of wavelength for a prior art broadband illumination source.
Figure 2G:
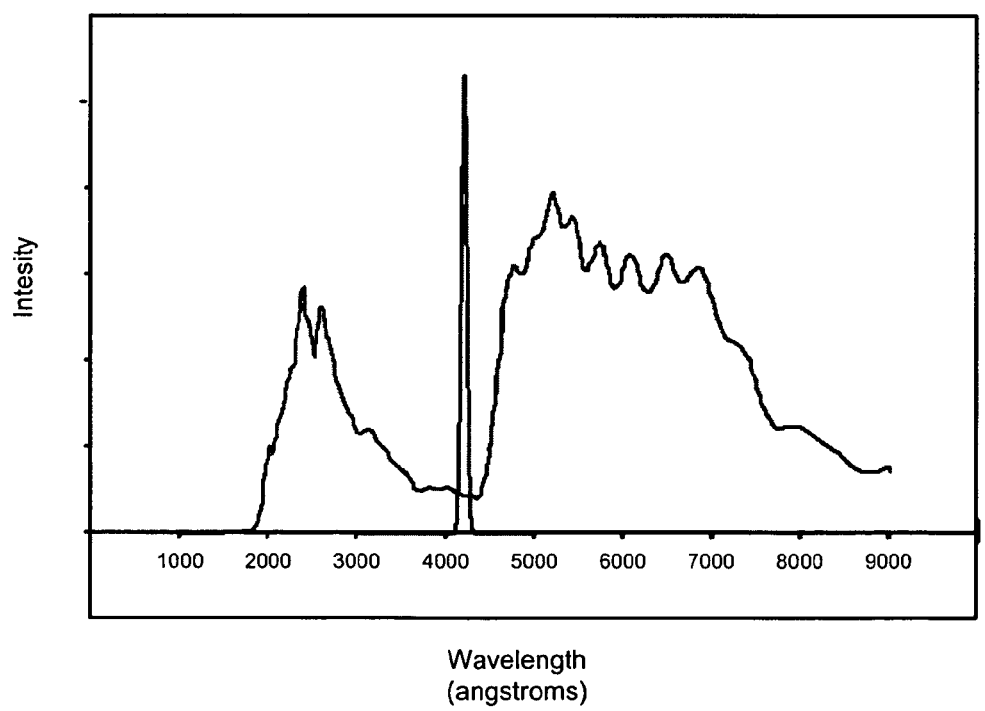
FIG. 2G is a graph showing illumination as a function of wavelength for the broadband illumination source of FIG. 2F supplemented by a single LED source.
Figure 2H:
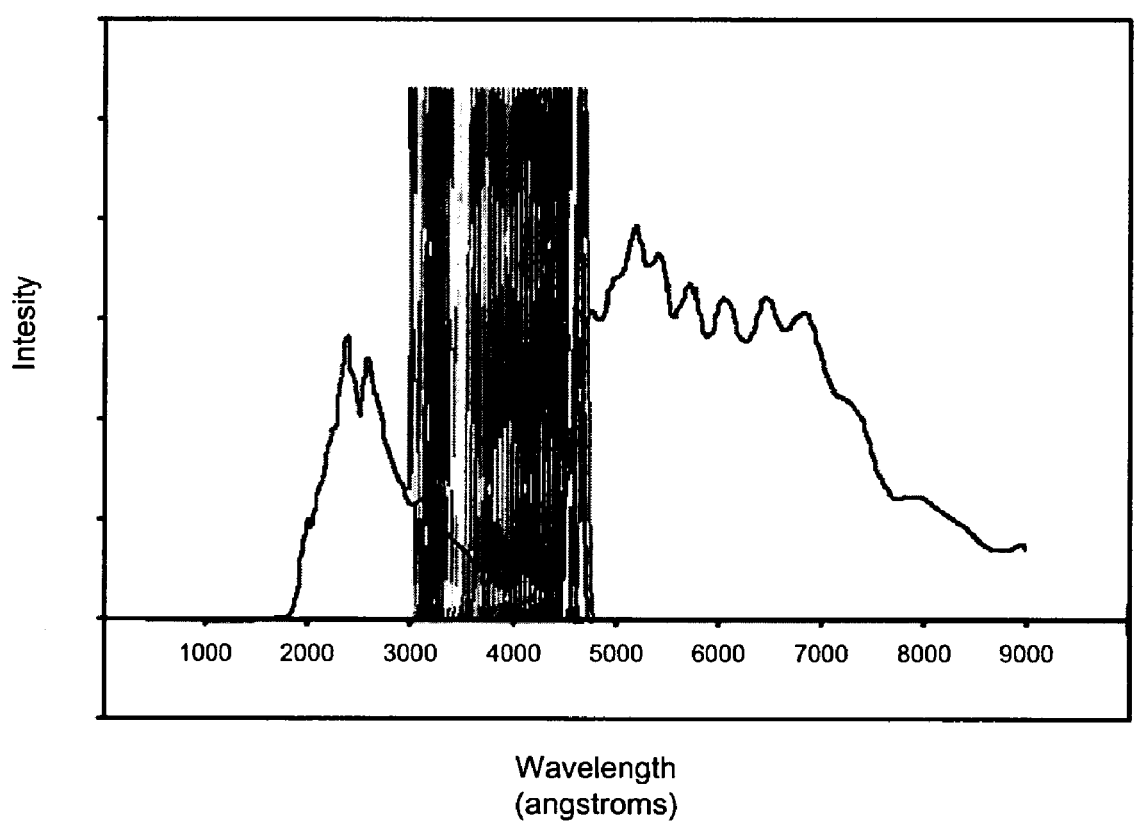
FIG. 2H is a graph showing illumination as a function of wavelength for the broadband illumination source of FIG. 2F supplemented by multiple LED sources.

FIGS. 2F through 2H illustrate an example where auxiliary light source 202 is implemented using a series of LED each emitting light at a different wavelength. FIG. 2F shows the un-supplemented illumination spectrum that is typically produced by the combination of UV source 204 and white light source 206. As may be appreciated, this spectrum source is characterized by a significant weakness near the 4000 Angstrom region. FIG. 2G shows the same illumination spectrum combined with the output of a single 405 nm LED. FIG. 2H continues the example by showing the original illumination spectrum combined with the output of a series of LEDs. In this case, the LED's have been selected, or temperature tuned to operate at a series of wavelengths. Their separate outputs are then combined, for example, using fiber bundle 208 to produce a supplemented probe beam. The overall effect is to provide significant enhancement across the region of the illumination spectrum in which intensity is lacking.

As can be appreciated, additional measurement information can be obtained by filling in the low intensity portion of the combined wavelength spectrum in and around 4000 angstroms. This could be achieved by using a plurality of individual laser diodes as mentioned above. In addition, efforts are being made to produce laser diodes with broader band emissions. These can include lasers of the type which include a phosphorus filter in the lens of the diode where the laser diode light excites the phosphorus to emit broad band light. It is believed that further advances in various broad band or white light diode lasers may allow the weak part of the combined spectrum (FIG. 2F) to be substantially filled in with only a few laser diodes.

While filling in the weak region of the combined spectrum with multiple diodes may be preferred from a measurement standpoint, it may only be necessary to utilize a single laser diode, thereby saving cost and reducing complexity. Taking for example FIG. 2G, simply providing a strong measurement line in a region where low noise measurements are significantly absent can provide enough additional information to resolve ambiguities about sample parameters.

Figure 3A:
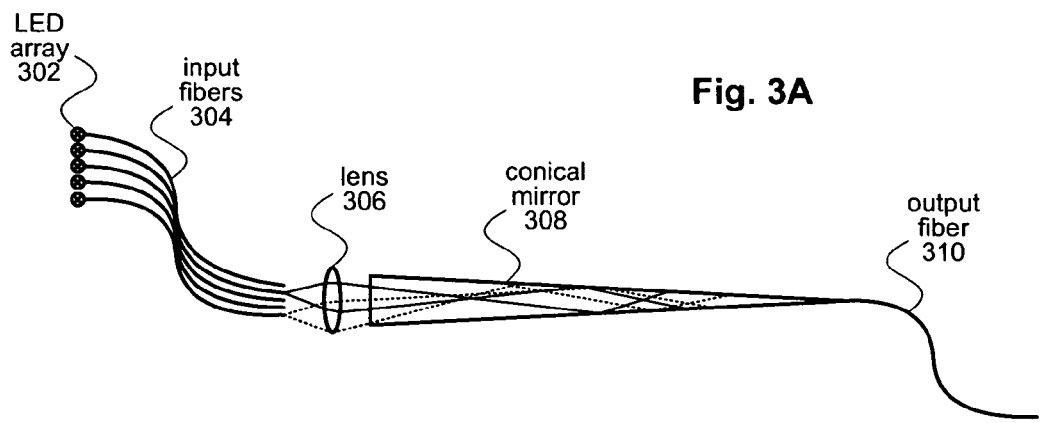
FIG. 3A is a diagram of a flat spectrum illumination source as provided by another embodiment of the present invention.

As shown in FIG. 3A, a second embodiment of the flat spectrum illumination source uses an array of light emitting diodes 302. The outputs of the LED array are combined into a single beam to create a flat spectrum probe beam. The process of combining the outputs of the LED array into a single beam may be performed using a range of optical components and configurations. For the specific example of FIG. 3A, the outputs of the LED array are first transported, using a series of optical fibers 304, to a lens 306. Lens 306 projects the LED outputs into a conical mirror 308. Mirror 308 combines the LED outputs and projects the combined beam into an output optical fiber 310.

Figure 3B:
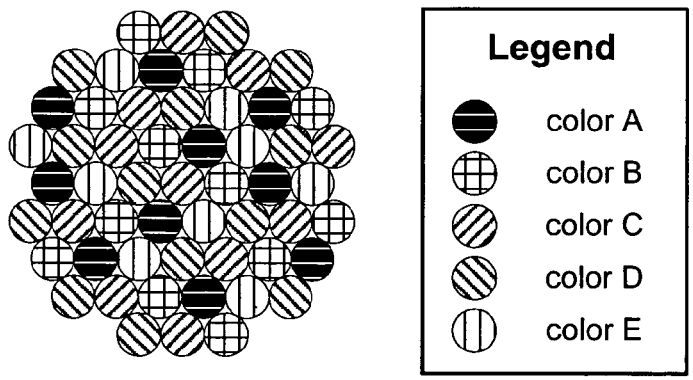
FIG. 3B is a diagram showing combination of separate LED outputs within the fiber of FIG. 3A.
Figure 3C:
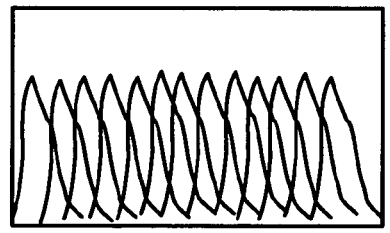
FIG. 3C is a graph showing illumination as a function of wavelength for the separate LEDs used in the illumination source of FIG. 3A.
Figure 3D:
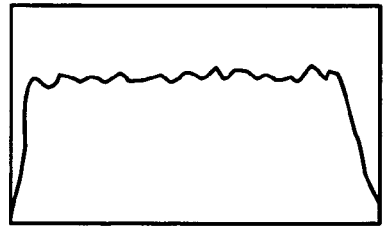
FIG. 3D is a graph showing illumination as a function of wavelength for the combined LEDs used in the illumination source of FIG. 3A.

As shown in FIG. 3B, the individual LEDs in array 302 in the LED are chosen to span a range of colors. Within the beam combiner, the outputs of the separate LEDs are mixed in an even distribution that appears as a single source. By controlling the current to each LED independently, the optical power out of the LEDs can be matched to create a flat spectrum. The outputs of the separate LEDs are shown in FIG. 3C and their combined effect is shown in FIG. 3D.

A third embodiment of the flat spectrum illumination source uses the LED array and beam combiner just described. In this case, the LED array is controlled to output a single color at a time. This is used in ellipsometers and reflectometers that scan a single color at time and eliminates the need to perform color balancing for the output of the individual LEDs. In addition, this embodiment does not require an order sorting filter to block second and higher orders from a diffraction grating that can lead to erroneous measurements and decreased signal to noise. Operation of the LED array is shown, for various colors in succession, in FIGS. 4A and 4D through 5A and 5D.

What is claimed is:

1. A device for optically inspecting and evaluating a sample, the device comprising:
    a light source for generating a probe beam, said light source include a first lamp having broadband emissions in the visible spectrum and a second lamp having broadband emissions in the ultraviolet spectrum and a laser diode emitting light in the blue visible region of the spectrum;
    optical elements for directing the probe beam to reflect off the sample;
    a detector for monitoring the reflected probe beam and generating output signals as a function of wavelength; and a processor for analyzing the sample based on the output signals.

2. A device as recited in claim 1, wherein the emissions from the first and second lamps and the laser diode are combined using beamsplitters.

3. A device as recited in claim 1, wherein the emissions from the first and second lamps and the laser diode are combined using optical fibers.

4. A device as recited in claim 3, wherein the optical fibers are in the form of a fiber bundle having an input end subdivided into respective portions for receiving light from the first and second lamps and said laser diode.

5. A device as recited in claim 1, wherein said first lamp is a tungsten lamp.

6. A device as recited in claim 1, wherein said second lamp is a deuterium lamp.

7. A device for optically inspecting and evaluating a sample, the device comprising:
   a first lamp having broadband emissions in the visible spectrum;
   a second lamp having broadband emissions in the ultraviolet spectrum;
   a narrowband light source for emitting narrowband output;
   means for combining the output from the first and second lamps and the narrowband light source to obtain a broadband probe beam, with the wavelength of the narrowband light source being selected to compensate for a reduced output intensity of the emissions from the first and second lamps;
   optical elements for directing the probe beam to reflect off the sample;
   a detector for monitoring the reflected probe beam and generating output signals as a function of wavelength; and
   a processor for analyzing the sample based on the output signals.

8. A device as recited in claim 7, wherein said combining means includes beamsplitters.

9. A device as recited in claim 7, wherein said combining means includes optical fibers.

10. A device as recited in claim 7, wherein said combining means includes a fiber bundle having an input end subdivided into respective portions for receiving light from the first and second lamps and the narrowband light source.

11. A device as recited in claim 7, wherein said first lamp is a tungsten lamp.

12. A device as recited in claim 7, wherein said second lamp is a deuterium lamp.

13. A device as recited in claim 12, wherein the narrowband light source is an LED.

14. A device as recited in claim 13, wherein said LED emits light in the blue visible region of the spectrum.

* * * * *